US006998158B2

(12) United States Patent
Hoerner et al.

(10) Patent No.: US 6,998,158 B2
(45) Date of Patent: Feb. 14, 2006

(54) MULTILAYER ELECTROMETRIC MATERIAL CONTAINING ACTIVE CHEMICAL SUBSTANCE, AND USES THEREOF

(75) Inventors: Pierre Hoerner, Montargis (FR);
Philippe Sonntag, Montargis (FR);
André Cheymol, Dange Saint Romain (FR); Raffi Krikorian, L'Isle Adam (FR)

(73) Assignee: Hutchinson, Paris (FR)

( * ) Notice: Subject to any disclaimer, the term of this patent is extended or adjusted under 35 U.S.C. 154(b) by 0 days.

(21) Appl. No.: 10/630,923

(22) Filed: Jul. 31, 2003

(65) Prior Publication Data
US 2004/0105943 A1 Jun. 3, 2004

(30) Foreign Application Priority Data
Jul. 31, 2002 (FR) .................................. 02 09734

(51) Int. Cl.
*B65D 1/00* (2006.01)
(52) U.S. Cl. .................... 428/35.7; 2/161.7; 2/168; 424/405; 604/292
(58) Field of Classification Search ............ 428/35.7, 428/36.8, 36.91, 492, 515; 2/161.7, 168; 424/405; 604/292
See application file for complete search history.

(56) References Cited

U.S. PATENT DOCUMENTS

| 5,338,565 A | 8/1994 | Shlenker et al. ............ 427/2.25 |
| 5,804,628 A | 9/1998 | Busnel et al. ................ 524/377 |
| 5,965,276 A | 10/1999 | Shlenker et al. ............ 428/492 |
| 6,020,070 A * | 2/2000 | Hoerner et al. .......... 428/423.1 |
| 6,391,326 B1 * | 5/2002 | Crepeau et al. ............ 424/405 |
| 2004/0105943 A1 * | 6/2004 | Hoemer et al. ............ 428/35.7 |

FOREIGN PATENT DOCUMENTS

| JP | 10128915 A | * 5/1998 |
| JP | 10287361 A | * 10/1998 |
| WO | 99/47589 | 9/1999 |

* cited by examiner

*Primary Examiner*—Sandra Nolan Rayford
(74) *Attorney, Agent, or Firm*—Morgan, Lewis & Bockius LLP

(57) ABSTRACT

The present invention relates to a multilayer material made from elastomers and containing one or more active substances dispersed in the form of droplets, and also to its uses, especially as a glove, a finger stall, a condom, a tape or dressings.

24 Claims, 3 Drawing Sheets

MULTILAYER ELECTROMETRIC MATERIAL CONTAINING ACTIVE CHEMICAL SUBSTANCE, AND USES THEREOF

The present invention relates to a multilayer material made from elastomers and comprising at least one layer containing one or more active substances dispersed in the form of droplets, and also to its uses, especially as a glove, a finger stall or condoms.

The various elastomeric materials usually used in the medical or paramedical field (especially hygiene) may be modified so as to be combined with active chemical substances, which have a protective effect, during the use of this material (gloves, finger stalls, condoms and various tapes and dressings). Specifically, not only in the cases of examination or surgery or in odontology, but also for protection against pathogens such as, for example, bacteria, viruses and fungal spores, a rupture or occasionally even simply the pores or a crack in the elastomeric membrane can result in contamination of the wearer of the said material by pricking with syringes, suture needles, trocars, bone splinters, etc.

Figure 1:
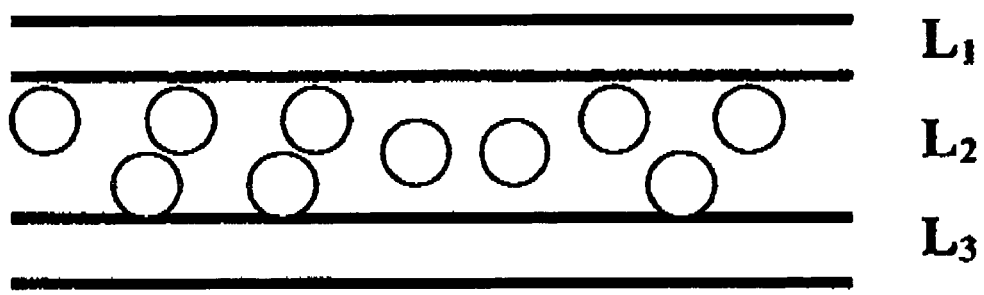
FIG. 1 shows a material with three separate layers $L_1$, $L_2$ and $L_3$.

Thus, elastomeric films in which are uniformly dispersed, in the form of liquid droplets, active chemical substances such as disinfectants for medical use, have already been proposed, especially in patent application EP-A-0 981 573. Such materials are generally in the form of three separate layers $L_1$, $L_2$ and $L_3$ as represented by FIG. 1 in which the layers $L_1$, and $L_3$ are outer barrier layers and $L_2$ represents an intermediate lava containine the active chemical substance(s) dispersed in the form of droplets.

In these materials, the liquid containing the active chemical substance(s) is uniformly and stably dispersed in the form of droplets and is thus available in the event of accidental rupture of the outer protective layer $L_1$ or $L_3$.

Unfortunately, such films do not always have the desired performance qualities. Firstly, the amount of active chemical substances coming into contact with the sharp object is quite often insufficient to ensure the desired properties, and secondly, the fluid is only placed in contact rather than expelled onto the blunt object, thus ensuring only partial wetting of the said object, resulting in low efficacy of devices of this type. This last point is all the more important since the geometry of the sharp object is often complex (hollow, bevelled needles, etc.).

It is thus in order to overcome these major problems that, in the course of its research, the Applicant has discovered, surprisingly, that the final characteristics of the multilayer material, such as the amount of active substance deposited on the blunt object and the speed of expulsion of the droplets of active substance, depend on the combination of the intrinsic characteristics of each of the constituent layers of the material.

According to the present invention, the term "intrinsic characteristics" means the mechanical characteristics (breaking stress and elastic constant) and size characteristics (thickness) of the formulated elastomers constituting each layer, and also, for the intermediate layer $L_2$, the degree of filling and the size of the droplets. In this invention, the intrinsic characteristics of each of the layers are adjusted by considering the multilayer material taken as a whole.

The inventors thus set themselves the aim of providing a multilayer elastomeric material containing at least one active substance, which is especially capable of being used in the medical or paramedical field for the manufacture of protective devices with improved performance qualities as regards the amount of active substance coming into contact with a blunt object in the event of perforation of the said device, and also as regards the speed with which this active substance comes into contact with the said blunt object compared with similar materials of the prior art.

A first subject of the invention is thus a multilayer elastomeric material comprising at least two outer barrier layers $L_1$ and $L_3$, respectively having a breaking stress $\sigma_1$ and $\sigma_3$ and a thickness $e_1$ and $e_3$, enclosing at least one intermediate layer $L_2$ consisting of an elastomeric matrix comprising at least one dispersion of droplets of at least one composition containing at least one active substance, the said intermediate layer $L_2$ having a breaking stress $\sigma_{2Tot}$ and a thickness $e_2$, characterized in that the mean diameter of the said droplets is greater than or equal to 10 μm and that the said material satisfies the following double inequality (1):

$$(\sigma_{2Tot} \cdot e_2) < (\sigma_1 \cdot e_1) \text{ and } (\sigma_{2Tot} \cdot e_2) < (\sigma_3 \cdot e_3) \qquad (I)$$

in which inequality:

$\sigma_{2Tot}$ represents the breaking stress of the charged elastomeric material constituting the layer $L_2$, $\sigma_1$, $\sigma_3$, $e_1$, $e_2$ and $e_3$ are as defined above.

In the inequalities defined above, $\sigma_{2Tot}$ is a function of the volume fraction $\phi v$ of the droplets incorporated into the layer $L_2$, and of the intrinsic characteristics of the elastomeric material constituting the matrix ($\sigma_2$). In this regard, $\phi v$ can, of course, be adjusted to satisfy the above inequalities concerning the breaking stress $\sigma_{2Tot}$.

By virtue of these particular characteristics, and when a pressure is exerted on the material in accordance with the invention with a sharp object, the intermediate layer $L_2$ gives way before the outer layers $L_1$ and $L_3$ and the droplets are expelled onto the sharp object after the outer barrier layer ($L_1$ and/or $L_3$) has been ruptured.

The inventors have in fact demonstrated that the rupture of the constituent layers of a multilayer material essentially depends on the resistance to the cutting or piercing force of each of the layers, which is proportional to the product of the breaking stress multiplied by the thickness for each of the layers. The breaking stress of the intermediate layer furthermore depends on the amount of composition containing the active substance included in this layer (volume fraction of liquid $\phi v$).

According to the invention, the breaking stresses $\sigma_1$, $\sigma_2$, $\sigma_{2Tot}$ and $\sigma_3$ are measured experimentally using a Zwick tensile testing machine, at a speed of 500 mm/minute and with specimens H2 according to standard NF EN455-2.

According to one advantageous embodiment of the invention, the product ($\sigma_{2Tot} \cdot e_2$) corresponds to the following double condition (II):

$$(\sigma_{2Tot} \cdot e_2) \leq (\sigma_1 \cdot e_1)/2 \text{ and } (\sigma_{2Tot} \cdot e_2) \leq (\sigma_3 \cdot e_3)/2 \qquad (II)$$

in which $\sigma_1$, $\sigma_{2Tot}$, $\sigma_3$, $e_1$, $e_2$ and $e_3$ have the same meanings as those given above.

The breaking stresses $\sigma_1$, $\sigma_2$ and $\sigma_3$ of each of the layers of the material in accordance with the invention, which may be identical or different, preferably range between 0.1 and 100 MPa and even more preferably between 5 and 40 MPa.

The thicknesses $e_1$, $e_2$ and $e_3$ of each of the layers of the material in accordance with the invention, which may be identical or different, preferably range between 25 and 500 µm approximately, this thickness being chosen as a function of the intended use of the said material.

As non-limiting examples, when the material in accordance with the invention is intended to be used for manufacturing condoms, then the thickness of each of the layers is about 25 µm; when it is used for manufacturing surgical gloves, then the thickness of each of the layers is about 100 µm and when it is used for manufacturing protective gloves, for example household gloves or refuse collectors' gloves, then the thickness of each of the layers is about 500 µm.

According to one preferred embodiment of the material in accordance with the invention, the mean diameter of the droplets dispersed in the layer $L_2$ is preferably between about 10 and 100 µm approximately.

Preferentially, the inventors have also demonstrated that the expulsion of the composition containing the active substance onto a blunt object perforating one of the two barrier layers $L_1$ or $L_3$ is also improved as a function of the viscoelasticity of the constituent materials of each layer, and more particularly of their elastic constant (E), i.e. $E_1$, $E_2$ and $E_3$, respectively.

Thus, according to one advantageous embodiment of the invention, the elastic constant of the constituent material of the intermediate layer $L_2$ is greater than that of the barrier layers $L_1$ and $L_3$ ($E_1$ and $E_3$), i.e. $E_2>\max(E_1, E_3)$.

According to the invention, the elastic constants of each of the layers $L_1$, $L_2$ and $L_3$, i.e. $E_1$, $E_2$ and $E_3$, respectively, are preferably between 0.1 and 50 MPa and even more preferably between 0.1 and 10 MPa for the layers $L_1$ and $L_3$ and between 0.5 and 50 MPa for the layer $L_2$; the values of $E_1$ and $E_3$ being identical or different.

According to the invention, the elastic constants are measured using a viscoanalyser of DMTA type (Dynamical Thermal Analysis such as the machine VA2000 from the company Metravib), which is capable of evaluating, in usual temperature ranges, the viscoelastic characteristics of the materials under consideration, at a frequency of 1 Hz (driven in the linear viscoelastic range), in traction-compression mode, according to the method described in standard NF EN ISO 527-3.

According to the invention, the elastomer(s) constituting the outer barrier layers $L_1$ and $L_3$ and also the intermediate layer $L_2$ are preferably chosen from natural rubber, polybutadiene, polyisoprene, polychloroprene, polyurethane, acrylic polymers or copolymers, silicone elastomers, SBR (Styrene Butadiene Rubber) copolymers, SBS (Styrene Butadiene Styrene) copolymers, isobutene-isoprene copolymers such as butyl rubber, NBR (Nitrile Butadiene Rubber) copolymers, x-NBR (carboxylated Nitrile Butadiene Rubber) copoymers, SIS (Styrene Isoprene Styrene) copolymers, SEBS (Styrene Ethylene Butylene Styrene) copolymers and blends thereof; it being understood that the nature of the elastomer(s) constituting each of the said layers may be identical to or different from each other. According to the invention, SIS and SEBS are preferred.

The characteristics of the elastomers (molar mass and crosslinking density (chemical and/or physical) are selected as a function of the final characteristics desired for the layers $L_1$ and $L_3$ and for the layer $L_2$, with the proviso that they satisfy, of course, the definitions given above.

In addition to the elastomers defined above, at least one of the barrier layers $L_1$ and $L_3$, and/or the intermediate layer $L_2$, may also contain one or more plasticizer(s) or flexibilizer(s) whose chemical nature and content are compatible with the intrinsic characteristics of the material as defined above.

When they are used, these plasticizers are preferably chosen from mineral oils, among which mention may be made especially of liquid paraffins, but may also be chosen from naphthalene-based oils or aromatic oils or mixtures of these products.

When they are used, the plasticizer(s) preferably represent(s) from 5 to 500 parts per 100 parts of elastomer constituting the layer in which they are present.

It should be noted that the chemical nature, the composition or the thickness of the layer $L_1$ is not necessarily equivalent to that of the layer $L_3$.

Finally, each layer $L_1$ or $L_3$ may, as a variant, result from the superposition of two or more sublayers of equivalent or non-equivalent chemical nature. The intrinsic characteristics of the layer $L_1$ or $L_3$ will then be those measured on the whole layer.

The intermediate layer $L_2$ serves as a matrix for the droplets of composition containing the active chemical substance(s) used.

According to the invention, the nature of this active substance may be chosen as a function of the properties that it is desired to give to the intermediate layer $L_2$. This active chemical substance may be chosen especially from anticorrosion agents, lubricants, chemical markers, phase-change products, energetic-particle (radiation) decelerators, agents with disinfecting power, odoriferous agents or moisturizers, dyes for detecting cuts, metallic particles, and mixtures thereof.

When the active chemical substance is a product with disinfecting power, it is preferably chosen from substances capable of causing a virtually instantaneous denaturation of proteins by simple contact, either by chemical reaction or by a physicochemical effect such as a modification of the surface tension. Among such substances, mention may be made especially of biocides, such as quaternary ammoniumns and more particularly dimethyldidecylammonium chloride and benzalkonium chloride, biguanides such as water-soluble salts of chlorhexidine, for instance chlorhexidine digluconate, phthalaldehyde, phenolic derivatives such as hexachlorophene or benzylic derivatives, formaldehyde, nonionic surfactants comprising at least one polyoxyethylene sequence such as octoxynol (Triton®X100), hexamidine, iodinated polyvinylpyrrolidone compounds, nonionic surfactants with virucidal activity, sodium and potassium dichromates and hypochlorites, and mixtures thereof.

In addition to the active chemical substance(s), the composition in the form of droplets may also contain one or more diluents for dissolving the said active chemical substance(s).

When it used, this diluent may be chosen especially from polyols and preferably from glycerol, ethylene glycol, polyethylene glycols that are liquid at room temperature or a temperature close to room temperature (between 20 and 30° C. approximately) and with a molar mass of between 62 (ethylene glycol) and 750 daltons (polyethylene glycol: PEG 750) and mixtures thereof, and also from any other compound that is compatible with the active chemical substance(s) used.

In addition, the composition in the form of droplets may also contain one or more additives for adjusting the final characteristics of the mixture, for instance dyes, surfactants or thickeners.

The composition in the form of droplets and containing the active substance may be in liquid (in the form of an emulsion), gelled form or contain crystalline portions (microspheres). When this composition is in the form of microspheres, they may also be coated with a thin film of protective polymer (microcapsules).

According to one particular embodiment of the invention, the intermediate layer $L_2$ may be formed from a superposition of two or more intermediate sublayers each comprising a dispersion of droplets, the nature of the active substances contained in each of the said sublayers being identical or different from one sublayer to another. In this case, the intrinsic characteristics of the layer $L_2$ will then be those measured on the whole layer.

According to another particular embodiment of the invention, the intermediate layer $L_2$ is formed by a single layer containing a dispersion of droplets containing active chemical substances that are different from one droplet to another.

Each of the layers constituting the elastomeric material in accordance with the invention may also contain other adjuvants conventionally used in the polymer industry, for instance antistatic agents, lubricants, antioxidants, colorants, processing agents or adhesion promoters depending on the particular properties that it is desired to impart thereto, provided, of course, that these adjuvants are compatible with each other and with the intrinsic characteristics of the said material as defined above.

Figure 2:
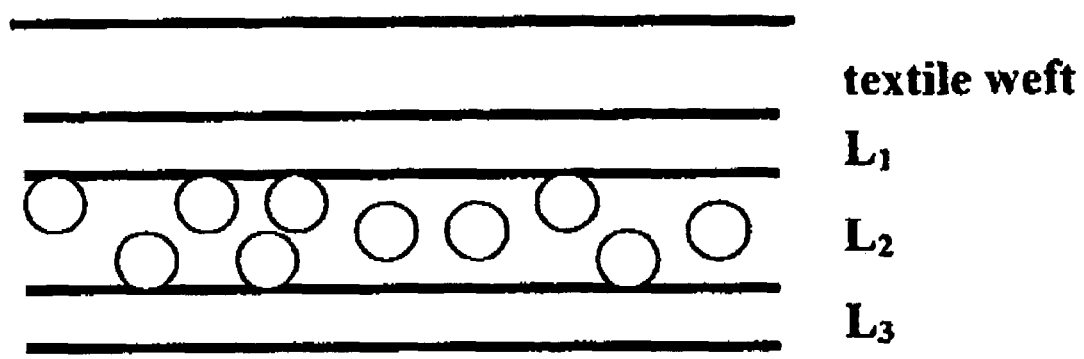
FIG. 2 shows a material with three separate layers $L_1$, $L_2$ and to and a textile weft.

According to one variant of the invention, the rnultiplayer material may be reinforced with an elastic textile weft of natural or synthetic organic fibres thus serving as a support for one of the two barrier layers $L_1$ or $L_3$. When the textile weft is adjacent to the barrier layer $L_1$, this type of multilayer material may be represented by FIG. 2.

The link between the various constituent layers of the material in accordance with the invention may optionally be provided by a bonding agent or by a chemical or physico-chemical modification of any one of the layers. However, such a treatment has no influence on the final characteristics of the material.

According to the invention, the expression "chemical modification" means either grafting or chemical attack, and "physicochemical modification" means bombardment of the surface of the film with ions, electrons or photons.

The multilayer elastomeric material in accordance with the invention may especially be in the form of gloves, finger stalls, condoms, tapes, dressings, etc.

A subject of the present invention is thus also the use of at least one multilayer elastomeric material as defined above for the manufacture of protective elastomeric articles such as gloves, finger stalls, condoms, tapes or dressings.

The manufacture of the multilayer material as defined above may be performed according to a process of successive dipping and evaporation operations on a form corresponding to the use intended for the said material, in organic solutions or aqueous dispersions (latex) of the chosen elastomer(s) so as to successively form the layers $L_1$, $L_2$ and $L_3$, the formation of the layer $L_2$ being performed, for example, by processes consisting:

either in preparing a stable emulsions formed from droplets of a liquid composition containing the active chemical substance(s) in a dissolution of the elastomer in a volatile solvent, as described especially in patent application EP-A-0 981 573;

or in preparing a dispersion of the said droplets in gelled form, or crystallized form (microspheres) in a dissolution of the elastomer in a volatile solvent, as described in patent application EP-A-771 837. Optionally, the microspheres may be coated with a thin film of protective polymer (microcapsules);

or in depositing the droplets, for example, in the form of microspheres or microcapsules onto the layer $L_1$ and/or $L_3$, and then in covering the said droplets with an elastomer, either in the form of a solution thereof in an organic solvent, or in the form of an aqueous dispersion (latex), or in solid form.

During this process, each dipping operation is followed by a period of evaporation, generally in a thermostatically regulated oven, during which the solvent or the water is removed.

When the multilayer material in accordance with the present invention comprises a support made of textile material, then the first dipping operation is performed with a porcelain form covered with a textile weft.

Besides the preceding arrangements, the invention also comprises other arrangements that will emerge from the description that follows, which refer to examples for preparing multilayer elastomeric materials in accordance with the invention, and also to a comparative example for preparing a multilayer material not in accordance with the invention.

It should be clearly understood, however, that these examples are given solely for the purposes of illustrating the subject of the invention, of which they do not in any way constitute a limitation.

EXAMPLE 1

Preparation of a Multilayer Elastomeric Material in Accordance With the Invention This example describes the preparation of a multilayer material made entirely from synthetic elastomer in solvent medium.

1) Preparation of the Multilayer Material

A first bath of elastomer in a solvent (cyclohexane) consisting of 20% by weight (relative to the solids) of a mix of SEBS copolymer sold under the trade name Kraton® G1652, by the company Kraton® Polymers, and of a mineral oil (Primol® 352, Esso company) used as plasticizer, is prepared. The elastomer/plasticizer mass proportions in this mixture are 100:30. This bath is used to make the barrier layers $L_1$ and $L_3$.

Moreover, and according to the process described in patent application EP-A-981 573, a bath of elastomer (SEBS: Kraton® G1652 at 20% by weight of solids in cyclohexane) containing a dispersion of droplets of active substance (benzalkonium chloride dissolved in ethylene glycol, in mass proportions of 1:9) stabilized with a particulate organic stabilizer, which is a polybutadiene-poly(ethylene oxide) diblock copolymer in a proportion of 5 parts per 100 parts of solution of benzalkonium chloride in ethylene glycol, is prepared.

The mean droplet diameter (measured using a optical microscope) in this dispersion is 30 $\mu$m. The volume fraction of the droplets $\phi v$ is 0.5 (relative to the solids after mixing with the elastomer dissolved in cyclohexane).

The multilayer material is then prepared by successive dipping operations of a porcelain form in the following manner:

1) formation of the barrier layer $L_1$: two successive dipping operations in the first elastomer bath;

2) formation of the intermediate layer $L_2$: three successive dipping operations in the second elastomer bath containing the dispersion of the active substance; and then 3) formation of the barrier layer $L_3$: two successive dipping operations in the first elastomer bath;

it being understood that each dipping step is immediately followed by a step of evaporating off the cyclohexane, first in the open air and then in an oven at a temperature of 40° C., until the solvent has completely evaporated off.

A multilayer material consisting of two identical barrier layers $L_1$ and $L_3$, each 175 µm thick, and of an intermediate layer $L_2$, 200 µm thick, containing a dispersion of droplets of benzalkonium chloride (the thicknesses are measured with a micrometric comparator) is thus obtained.

2) Characterization of the Multilayer Material

In order to determine the intrinsic characteristics of each of the layers constituting this material, two separate elastomeric films are prepared by:
- firstly dipping a first porcelain form in the first elastomer bath (according to the technique described above in Step 1) for the preparation of the multilayer material) so as to produce a monolayer material consisting only of a layer $L_1$;
- secondly, dipping a second porcelain form in the second elastomer bath (according to the technique described above in Step 2) for the preparation of the multilayer material) so as to produce a monolayer material consisting only of a layer $L_2$ The separate layers $L_1$ and $L_2$ thus prepared were then studied in order to measure their intrinsic characteristics.

For each of the layers $L_1$ and $L_2$, the breaking stresses were measured using a tensile testing machine (Zwick) on specimens of H2 type, at a speed of 500 mm/minute, in accordance with standard NF EN455-2.

The elastic constants are measured using a VA2000 viscoanalyser (Metravib R. D. S, Limonest, France) on rectangular specimens of the layers $L_1$ and $L_2$, 20×50 mm in size, in traction-compression mode, in accordance with the method described in standard NF EN ISO 527-3.

The amount of active chemical substance expelled onto a needle during perforation of the glove is evaluated on the multilayer material, by means of a standardized test consisting in:
- cutting the multilayer material along a vertical cutting plane $L_1$, $L_2$, $L_3$, under liquid nitrogen,
- backing the cutting plane onto a glass slide,
- placing the assembly in the field of a reflecting microscope (Questar),
- pricking the multilayer material with a hollow needle 0.7 mm in diameter, filled with ultrapure water, at a pricking speed of 15 cm/s,
- measuring the speed of expulsion of the benzalkonium chloride under the field of the microscope using a video camera,
- analytically assaying the amount of benzalkonium chloride deposited on the needle using a capillary electrophoresis device.

3) Results

The characteristics of the multilayer material are summarized in Table I below:

TABLE I

| Layers | Breaking stress σ (in Mpa) | Elastic constant E (in Mpa) | Product (σ · e) (in Pa · m) |
|---|---|---|---|
| $L_1$ | 25 | 2 | 4375 |
| $L_2$ | 9 [a] | 7 | 1800 |
| $L_3$ | 25 | 2 | 4375 |

[a] the value given is the breaking stress of the elastomeric layer charged with benzalkonium chloride.

The amount of benzalkonium chloride deposited on the needle is evaluated at 1 µg; the speed of expulsion is estimated as 5 m/s.

EXAMPLE 2

Preparation of a Multilayer Material in Accordance With the Invention

The aim of this example is to illustrate the preparation of a "hybrid" material made from natural rubber and synthetic elastomer via a water and solvent mixed process.

1) Preparation of the Multilayer Material

In this case, the said material is obtained by successive dipping operations of a porcelain form in an aqueous dispersion of natural rubber (latex) to form the two barrier layers $L_1$ and $L_3$ and in a solution of synthetic elastomer in cyclohexane, the said solution containing a dispersion of active substance to form the layer $L_2$.

a) Preparation of the Barrier Layers $L_1$ and $L_3$

The barrier layers are formed by superposition of two sublayers.

The first sublayer is formed by dipping (twice) a porcelain form in a bath of nitrile latex (x-NBR: butadiene-acrylonitrile-methacrylic acid copolymer, sold by the company Polymer Latex) at 50% (solids) also comprising 10% zinc oxide, 2% zinc diethyldithiocarbamate (ZDEC) and 1.5% sulphur.

The second sublayer is formed by dipping (once) the form in a mixture of natural latex (NR) and of nitrile latex x-NBR, in a mass proportion of 75:25. The nitrile latex is the same as that used above to form the first sublayer. The natural latex (Heveatex) is formulated with 1% sulphur and 0.8% ZDEC.

The solids content of the nitrile latex/natural latex mixture is about 45%.

b) Formation of the Layer $L_2$

This is prepared as described above in Example 1.

A multilayer material consisting of two identical barrier layers $L_1$ and $L_3$ each 250 µm thick and of an intermediate layer $L_2$, 200 µm thick, containing a dispersion of droplets of benzalkonium chloride, is thus obtained.

Each dipping step is immediately followed by a step of evaporating off the water, first in the open air and then in an oven at a temperature of 40° C. (evaporation of the cyclohexane for the layer $L_2$) or at 60° C. (evaporation of the water for the layers $L_1$ and $L_3$), until the cylcohexane and the water have completely evaporated off.

The final multilayer material is then vulcanized at 80° C. for 2 hours.

Figure 3:
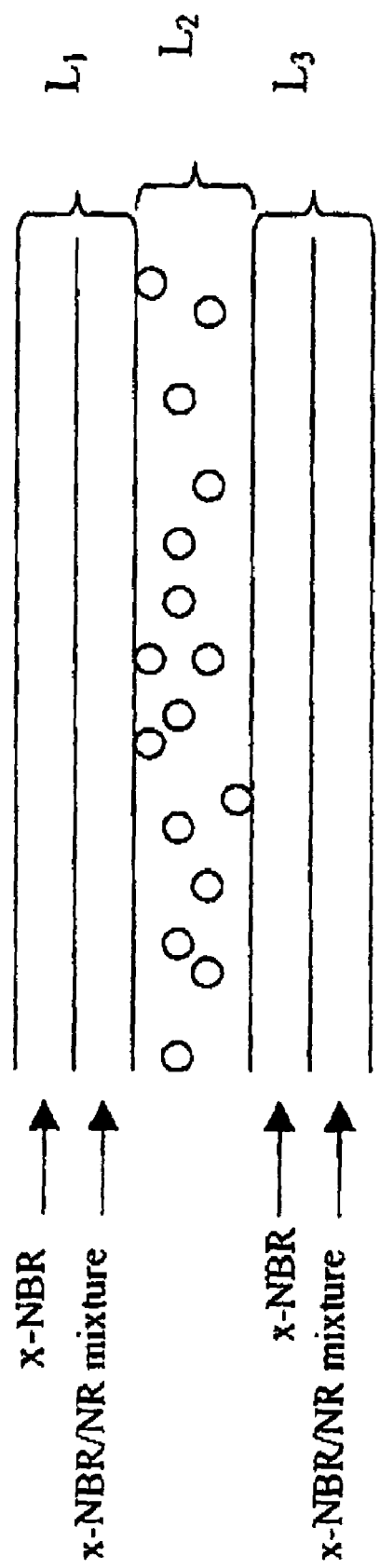
FIG. 3 shows a multilayer material produced by Example 2.

The structure of the final material as produced according to this example is represented in FIG. 3.

The multilayer material thus prepared is then characterized according to the methods described above in Example 1.

The characteristics obtained are given in Table II below:

TABLE II

| Layers | Breaking stress σ (in Mpa) | Elastic constant E (in Mpa) | Product (σ · e) (in Pa · m) |
|---|---|---|---|
| $L_1$ | 12 | 3 | 3000 |
| $L_2$ | 9 [a] | 7 | 1800 |
| $L_3$ | 12 | 3 | 3000 |

[a] the value given is the breaking stress of the elastomeric layer charged with benzalkonium chloride.

The amount of benzalkonium chloride deposited on the needle after the perforation test under the conditions described above in Example 1 is evaluated as 0.6 µg. The speed of expulsion is evaluated as 3 m/s.

COMPARATIVE EXAMPLE 3

Preparation of a Multilayer Material Not in Accordance With the Invention

This counterexample illustrates the preparation of a multilayer material based on synthetic elastomers of SEBS type but whose characteristics do not correspond to the double inequality (1) as defined according to the present invention.

1) Preparation of the Multilayer Material

The multilayer material is entirely made from dissolutions of SEBS in cyclohexane. The various elastomer baths used to make the layers $L_1$ and $L_3$ are as follows:

Barrier layers $L_1$ and $L_3$: elastomer bath consisting of 20% by weight (relative to the solids) of a mixture of SEBS copolymer sold under the trade name Kraton® G1652 by the company Kraton Polymers, and of a mineral oil (Primol® 352, Esso company) used as plasticizer, dissolved in cyclohexane. The elastomer/plasticizer mass proportions in this mixture are 100:30.

Intermediate layer $L_2$: elastomer bath consisting of 20% by weight (relative to the solids) of a mixture of SEBS copolymer sold under the trade name Kraton® G1654 by the company Kraton® Polymers, and of a mineral oil (Marcol® 82, Esso company) used as plasticizer, dissolved in cyclohexane. The elastomer/plasticizer mass proportions in this mixture are 100:50. This elastomer bath contains a dispersion of droplets of active substance (benzalkonium chloride dissolved in ethylene glycol, in mass proportions of 1:9) stabilized with a particulate organic stabilizer, which is a polybutadiene-poly(ethylene oxide) diblock copolymer in a proportion of 5 parts per 100 parts of solution of benzalkonium chloride in ethylene glycol.

The mean droplet diameter (measured using an optical microscope) in this dispersion is 30 µm. The volume fraction of the droplets φv is 0.3 (relative to the solids content after mixing with the elastomer dissolved in cyclohexane).

A multilayer material consisting of two identical barrier layers $L_1$ and $L_3$ each 150 µm thick and of an intermediate layer $L_2$, 250 µm thick, containing a dispersion of droplets of benzalkonium chloride (the thicknesses are measured using a micrometric comparator) is thus obtained.

The multilayer material thus prepared is then characterized according to the methods described above in Example 1.

The characteristics obtained are given in Table III below:

TABLE III

| Layers | Breaking stress σ (in Mpa) | Elastic constant E (in Mpa) | Product (σ · e) (in Pa · m) |
|---|---|---|---|
| $L_1$ | 25 | 2 | 3775 |
| $L_2$ | 16 [a] | 1 | 4000 |
| $L_3$ | 25 | 2 | 3775 |

[a] the value given is the breaking stress of the elastomeric layer charged with benzalkonium chloride.

A material whose intrinsic characteristics do not satisfy the double inequality (I) defined above, since the product $(\sigma_{2Tot} \cdot e^2)$ of the intermediate layer $L_2$ is greater than that of each of the barrier layers $L_1$ and $L_3$, is thus obtained.

The amount of benzalkonium chloride deposited on the needle after the perforation test under the conditions described above in Example 1 is evaluated as 0.1 µg, which corresponds to an amount that is about 10 times less than that of Example 1. The speed of expulsion is evaluated as 1 m/s, which corresponds to a speed that is about 5 times slower than that of Example 1.

This set of results shows that the materials in accordance with the invention, i.e. the multilayer materials in which the intrinsic characteristics of each of the layers satisfy the double inequality (I) as defined above, show improved performances as regards the amount of active substance coming into contact with a needle in the event of perforation of the said material, and also as regards the speed with which this active substance comes into contact with the said needle.

What is claimed is:

1. A multilayer elastomeric material comprising:
   at least two outermost elastomeric barrier layers $L_1$ and $L_3$, respectively having a breaking stress $\sigma_1$ and $\sigma_3$, a thickness $e_1$ and $e_3$, and an elastic constant $E_1$ and $E_3$, enclosing
   at least one intermediate layer $L_2$ consisting of an elastomeric matrix comprising at least one dispersion of droplets of at least one composition containing at least one active substance, the intermediate layer $L_2$ having a breaking stress $\sigma_{2Tot}$, a thickness $e_2$, and an elastic constant $E_2$,
   wherein the mean diameter of the droplets is at least 10 µm and that the material satisfies the following double inequality (I):

$$(\sigma_{2Tot} \cdot e_2) < (\sigma_1 \cdot e_1) \text{ and } (\sigma_{2Tot} \cdot e_2) < (\sigma_3 \cdot e_3) \qquad (I)$$

in which:
$\sigma_{2Tot}$ represents the breaking stress of the charged elastomeric material constituting the layer $L_2$, and
$\sigma_1$, $\sigma_3$, $e_1$, $e_2$ and $e_3$ are as defined above.

2. The material according to claim 1, wherein the product $(\sigma_{2Tot} \cdot e_2)$ corresponds to the following double condition (II):

$$(\sigma_{2Tot} \cdot e_2) \leq (\sigma_1 \cdot e_1)/2 \text{ and } (\sigma_{2Tot} \cdot e_2) \leq (\sigma_3 \cdot e_3)/2 \qquad (II)$$

in which $\sigma_1$, $\sigma_{2Tot}$, $\sigma_3$, $e_1$, $e_2$ and $e_3$ are as defined in claim 1.

3. The material according to claim 1, wherein the breaking stresses $\sigma_1$, $\sigma_2$ and $\sigma_3$ of each of the layers of the material, which may be identical or different, range between 0.1 and 100 MPa.

4. The material according to claim 1, wherein the thicknesses $e_1$, $e_2$ and $e_3$ of each of the layers of the material, which may be identical or different, range between 25 and 500 µm.

5. The material according to claim 1, wherein the mean diameter of the droplets is between 10 and 100 µm.

6. The material according to claim 1, wherein the elastic constant, $E_2$, of the constituent material of the intermediate layer $L_2$ is greater than each of the elastic constants, $E_1$ and $E_3$, of the barrier layers $L_1$ and $L_3$, respectively.

7. The material according to claim 6, wherein the elastic constants $E_1$, $E_2$ and $E_3$ of each of the layers $L_1$, $L_2$ and $L_3$, respectively, are between 0.1 and 50 MPa, and the values of $E_1$ and $E_3$ being identical or different.

8. The material according to claim 7, wherein the elastic constants of the layers $L_1$ and $L_3$, which may be identical or different, are between 0.1 and 10 MPa and the elastic constant of the layer $L_2$ is between 0.5 and 50 MPa.

9. The material according to claim 1, wherein the elastomer(s) constituting the barrier layers $L_1$ and $L_3$ and also the intermediate layer $L_2$ are chosen from natural rubber, polybutadiene, polyisoprene, polychloroprene, polyurethane, acrylic polymers or copolymers, silicone elastomers, SBR (Styrene Butadiene Rubber) copolymers, SBS (Styrene Butadiene Styrene) copolymers, SEBS (Styrene Ethylene Butylene Styrene) copolymers, isobutene-isoprene copolymers, NBR (Nitrile Butadiene Rubber) copolymers, x-NBR (carboxylated Nitrile Butadiene Rubber) copolymers, SIS (Styrene Isoprene Styrene) copolymers and blends thereof.

10. The material according to claim 9, wherein the elastomers are chosen from SIS and SEBS.

11. The material according to claim 1, wherein at least one of the barrier layers $L_1$ and $L_3$, and optionally the intermediate layer $L_2$, also contains one or more plasticizer(s) or flexibilizer(s).

12. The material according to claim 11, wherein the plasticizer(s) represent(s) from 5 to 500 parts per 100 parts of elastomer constituting the layer in which they are present.

13. The material according to claim 1, wherein each layer $L_1$ or $L_3$ results from the superposition of two or more sublayers of equivalent or non-equivalent chemical nature.

14. The material according to claim 1, wherein the active chemical substance is chosen from anticorrosion agents, lubricants, chemical markers, phase-change products, energetic-particle (radiation) decelerators, agents with disinfecting power, odoriferous agents or moisturizers, dyes for detecting cuts, metallic particles, and mixtures thereof.

15. The material according to claim 14, wherein the active chemical substance is chosen from biocides, biguanides, phthalaldehyde, phenolic derivatives, formaldehyde, nonionic surfactants comprising at least one polyoxyethylene sequence, hexamidine, iodinated polyvinylpyrrolidone compounds, nonionic surfactants with virucidal activity, sodium and potassium dichromates and hypochlorites, and mixtures thereof.

16. The material according to claim 1, wherein the composition in the form of droplets also contains one or more diluents for dissolving the active chemical substance(s).

17. The material according to claim 1, wherein the dispersion of droplets is in liquid or gelled form or contains crystalline parts.

18. The material according to claim 1, wherein the intermediate layer $L_2$ is formed from a superposition of two or more intermediate sublayers each comprising a dispersion of droplets, the nature of the active substances contained in each of the sublayers being identical or different from one sublayer to another.

19. The material according to claim 1, wherein the intermediate layer $L_2$ is formed by a single layer containing a dispersion of droplets containing active chemical substances that are different from one droplet to another.

20. A glove, comprising the elastomeric material of claim 1.

21. A finger stall, comprising the elastomeric material of claim 1.

22. A condom, comprising the elastomeric material of claim 1.

23. A tape, comprising the elastomeric material of claim 1.

24. A dressing, comprising the elastomeric material of claim 1.

* * * * *